United States Patent [19]

Steer

[11] Patent Number: 4,671,272

[45] Date of Patent: Jun. 9, 1987

[54] LOOP OSTOMY APPLIANCE

[75] Inventor: Peter L. Steer, Surrey, England

[73] Assignee: Craig Medical Products, Limited, Sussex, England

[21] Appl. No.: 754,385

[22] Filed: Jul. 12, 1985

[51] Int. Cl.4 ............................................. A61B 17/00
[52] U.S. Cl. ................................. 128/303 R; 128/352; 128/353
[58] Field of Search .................... 128/352, 353, 303 R

[56] References Cited

U.S. PATENT DOCUMENTS 3,779,247 12/1973 Nolan et al. .................... 128/303 R
4,434,795 3/1984 Mericle ........................... 128/303 R

OTHER PUBLICATIONS

Sur-fit Ostomy Product Brochure, Nov. 1981.

*Primary Examiner*—C. Fred Rosenbaum
*Assistant Examiner*—John D. Ferros
*Attorney, Agent, or Firm*—Lawrence S. Levinson; Sanford J. Asman

[57] ABSTRACT

An integrally formed single piece loop ostomy appliance includes a central rod portion, a cross piece transverse to the rod portion at one end, and a displaceable end piece at the other end, displaceable between a first position which extends in the same general direction as the rod portion and a second position transverse to the rod portion. The end piece comprise a catch disposed to be in locking engagement with a recess in the rod portion when the end piece is moved to the second position. The end piece further comprises first and second spaced apart walls partially forming an aperture and adapted to be squeezed toward one another to release the catch from the recess. The loop ostomy appliance is preferably made of plastic, e.g. polypropylene.

5 Claims, 4 Drawing Figures

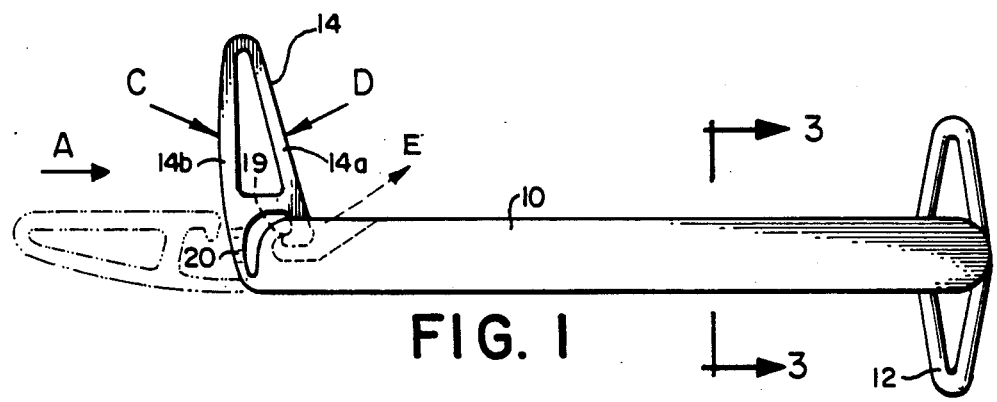
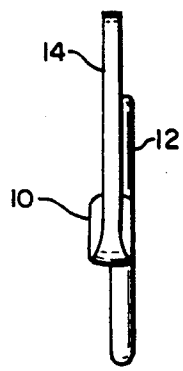
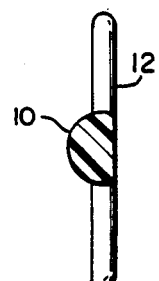
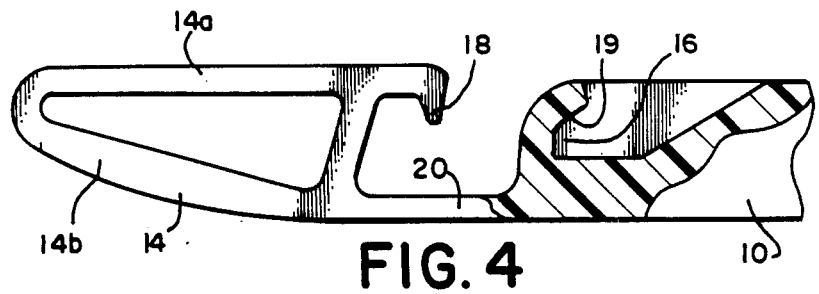

LOOP OSTOMY APPLIANCE

BACKGROUND OF THE INVENTION

This invention relates to a loop ostomy appliance.

Some abdominal surgery operations require a length of the bowel to be maintained temporarily outside the body. For this purpose it has been customary to employ an ostomy appliance in the form of a rod which is inserted through a loop of the bowel. The bowel may then be cut or slit at the loop forming an opening through which temporary discharge can take place. The external surface of the bowel is highly slippery, and the danger of dislogment of the rod is a serious problem.

SUMMARY OF THE INVENTION

According to the present invention, there is provided a loop ostomy appliance comprising a rod portion, a cross piece at or near one end of the rod portion, and a displaceable end piece integral with and at the other end of the rod portion, the end piece having a catch and being displaceable between a first position, in which the end piece extends in the same general direction as the rod and a second position in which it can be held by engagement of the catch with the rod, the end piece in its second position being generally transverse to the rod.

In the preferred embodiment, there is a recess in the rod portion into which the catch can engage.

According to a specially preferred embodiment of the invention, the end piece has a central hole and is shaped so that pressure on walls surrounding the hole deforms the end piece and bends a catch portion thereof to a position in which the end piece can be released from the rod portion.

The invention will be better understood from the following nonlimiting description of an example thereof given with reference to the accompanying drawings in which:

BRIEF DESCRIPTION OF THE DRAWINGS

FIG. 1 is a plan view of one example of the invention showing the catch portion in its first (dotted lines) and second (solid lines) positions;

FIG. 2 is an end elevation looking in the direction of the arrow A in FIG. 1;

FIG. 3 is a section on the line 3—3 of FIG. 1.

FIG. 4 is a view on an enlarged scale of part of FIG. 1.

DETAILED DESCRIPTION OF THE DRAWINGS

The loop ostomy appliance illustrated in FIGS. 1-4 includes a rod portion 10, a cross-piece 12 at or near one end of the rod portion 10, and a displaceable end piece, also referred to herein as a hinged tab, which is integral with and at the other end of the rod portion 10. The hinged tab is indicated by reference numeral 14.

In FIG. 1 two possible positions of the hinged tab 14 are shown, the first position being dotted wherein the end piece extends in the same general direction as the rod portion 10, and the second position being shown in full lines which is the working or operational position once the bowel is looped over the rod portion 10.

Due to the arrangement of a recess 16 in the rod portion 10 and a detent catch 18 on the end piece 14 which engages with a wall 19 of the recess 16, the end piece 14 is securely maintained, when desired, in its working position (FIG. 1 full lines). The end piece is swung back to the position illustrated in FIG. 4 when it is required to remove the loop ostomy appliance. This is achieved by squeezing the end piece 14 between finger and thumb, so applying pressure to the walls 14a and 14b in the directions of the respective arrows C and D (FIG. 1) which causes the catch 18 to be deformed in the direction of the arrow E so that it is readily disengaged from the recess 16 in the rod portion 10.

The appliance is preferably made from polypropylene, and the end piece 14 is hinged to the rod portion 10 by a web 20 which constitutes an integral hinge.

An advantage of the appliance according to the invention is that it is in one piece to ensure maximum security; detachment of parts or loss of parts is not possible. The intetral hinge will flex up to at least 1000 times without failure.

What is claimed is:

1. A loop ostomy appliance comprising:
   a rod portion,
   a cross portion at one end thereof, and
   a displaceable end piece at the other end of said rod portion, all formed integrally as one piece; said rod portion having a recess at the other end thereof, said displaceable end piece displaceable between a first position in which said end piece extends in the same general direction as the rod portion and a second position generally transverse to said rod portion, said end piece further comprising a catch means for locking engagement with said recess in said rod portion when said end piece is in said second position.

2. The loop ostomy appliance of claim 1 wherein said end piece comprises first and second flexible spaced apart walls partially defining an aperture therebetween, said first and second walls adapted to be squeezed toward one another to release said catch means from said recess.

3. The loop ostomy appliance of claim 2 wherein said catch means forms an-extension of said first wall beyond said aperture.

4. The loop ostomy appliance of claim 3 wherein said end piece is formed with said rod portion by an integrally formed hinge.

5. The loop ostomy appliance of claim 4 wherein said loop ostomy appliance is comprised of polypropylene.

* * * * *